United States Patent [19]

Hirose et al.

[11] 4,008,286

[45] Feb. 15, 1977

[54] PROCESS FOR PREPARING GLYCOLS

[75] Inventors: Isao Hirose; Hiroyuki Okitsu, both of Iwakuni, Japan

[73] Assignee: Teijin Limited, Osaka, Japan

[22] Filed: Feb. 20, 1976

[21] Appl. No.: 659,853

[30] Foreign Application Priority Data

Feb. 20, 1975 Japan .............................. 50-20351
Feb. 5, 1976 Japan .............................. 51-10816

[52] U.S. Cl. ..................... 260/635 H; 260/497 R; 260/597 R; 260/634; 260/636; 260/659 R
[51] Int. Cl.² ......................................... C07C 29/02
[58] Field of Search ....................... 260/636, 635 H
[56] References Cited

UNITED STATES PATENTS

| 2,911,437 | 11/1959 | Keith ............................. 260/635 H |
| 3,140,303 | 7/1964 | De La Mare et al. ......... 260/635 H |
| 3,360,548 | 12/1967 | Clark et al. .................... 260/635 H |
| 3,789,065 | 1/1974 | Kollar ............................. 260/635 H |

FOREIGN PATENTS OR APPLICATIONS 45-36291    1970    Japan ............................ 260/635 H

*Primary Examiner*—Joseph E. Evans
*Attorney, Agent, or Firm*—Wenderoth, Lind & Ponack

[57] ABSTRACT

A process for making glycols comprising contacting an aliphatic olefin with 2–4 carbon atoms with an aqueous medium containing i. at least one cation selected from the group consisting of copper ions and iron ions, and
ii. an anion which at least includes a bromine ion and can solubilize copper and/or iron at 100°–200° C., to form a glycol corresponding to the starting olefin, which is characterized in that the concentrations of the cation and anion and the ratio therebetween are controlled under specific conditions.

13 Claims, No Drawings

PROCESS FOR PREPARING GLYCOLS

This invention relates to a process for oxidizing olefins with molecular oxygen by liquid-phase reaction in an aqueous medium composed chiefly of water, ultimately making the glycols corresponding to the olefins.

More particularly, the invention relates to a process comprising contacting an aliphatic olefin with 2–4 carbon atoms with an aqueous medium containing
 i. at least one cation selected from the group consisting of copper and iron ions, and
 ii. an anion which at least includes a bromine ion and can solubilize copper and/or iron at 100°–200° C., thereby making a glycol corresponding to the olefin.

Recently numbers of proposals were made as to preparation of glycols or esters thereof by oxidizing olefins at liquid phase provided by water, acetic acid, and the like, by the catalytic action of noble metal salts or special metal salt. Those reactions have a common advantage over the so-called vapor phase oxidation heretofore widely adopted for industrial scale production of glycols, in that the reaction conditions are mild and the yields of the product is markedly high.

However those processes are also subject to various defects, such as that because they use expensive noble metal salt, e.g., palladium salt or special metal salt of high reactivity such as tellurium or thallium salt, care must be taken to prevent escape of the catalyst from the reaction system; the loss of auxiliary material such as acetic acid or nitric acid becomes by no means negligible; or the glycol is obtained in the ester form with acetic acid; or, that the formation of by-product must be inhibited by for example, reducing the production rate of glycol.

We have previously proposed a process for making glycols from the corresponding olefins, using copper and iron salts as the catalyst (Japanese Official Patent Gazette, Publication No. 36291/70).

The process we proposed has the advantage over conventional processes that simply by contacting an olefin with molecular oxygen in an aqueous solution of copper salt and/or iron salt, the corresponding glycol can be easily and directly obtained.

The reaction rate of the process, however, is relatively low, and in that one point the process cannot be said very practically advantageous.

Also as a similar method it was proposed to make glycols by contacting olefins with an aqueous medium containing copper and bromine sources and molecular oxygen (West German published Pat. No. 1,948,838). However, so fas as can be known from the disclosed reaction conditions, particularly from the Examples, the glycol yield is low even when the technique known per se of using molecular bromine as a reactant is concurrently employed, and the rate of reaction again is low. Thus the process can hardly be satisfactory for practical purposes.

Accordingly, a primary object of the present invention is to provide a process for making glycols directly from olefins in an aqueous medium at both high reaction rate and selectivities, without the use of expensive noble metal salt or special metal salt of high reactivity proposed by conventional processes.

An additional object of the invention is to provide a process for making from olefins the corresponding glycols continuously, at both high reaction rate and selectivities, using as the catalyst cheap metal salt which never causes environmental pollution if escaped from the reaction system.

Still other objects and advantages will become apparent in the following specification.

The foregoing objects and advantages of the invention can be achieved by the process comprising contacting an aliphatic olefin having 2–4 carbon atoms with an aqueous medium containing
 i. at least one cation selected from copper and iron ions, and
 ii. an anion which at least includes a bromine ion and can solubilize copper and/or iron, at 100°–200° C., thereby making a glycol corresponding to said olefin, characterized in that the concentrations of the cation and anion as well as the ratio between the two are controlled to satisfy the following conditions:

I. when the cation in the aqueous medium is a copper ion, $$0.4 \leq [Cu^t] \leq 2.5 \quad (1)$$

$$0.8 \leq [Br^-] \leq 4.0 \quad (2)$$

$$1.75 [Cu^t] \leq [A^t] \leq 2.0 [Cu^t] \quad (3)$$

$$0.8 [Cu^t] \leq [Br^-] \leq 1.95 [Cu^t] \quad (4)$$

II. when the cation in the aqueous medium is an iron ion, $$0.3 \leq [Fe^t] \leq 2.0 \quad (5)$$

$$0.5 \leq [Br^-] \leq 6.0 \quad (6)$$

$$2.0 [Fe^t] \leq [A^t] \leq 3.0 [Fe^t] + 4.0 \quad (7)$$

$$0.7 [Fe^t] \leq [Br^-] \leq 3.0 [Fe^t] + 1.0 \quad (8)$$

and

III. when the cation in the aqueous medium consists of copper and iron ions, $$0.05 \leq [Cu^t] + [Fe^t] \leq 1.5 \quad (9)$$

$$0.01 \leq [Cu^t] \quad (10)$$

$$0.01 \leq [Fe^t] \quad (11)$$

$$0.5 \leq [Br^-] \leq 4.0 \quad (12)$$

$$2.0\{[Cu^t]+[Fe^t]\} \leq [A^t] \leq 3.5\{[Cu^t]+[Fe^t]\}+4.0 \quad (13)$$

$$1.0\{[Cu^t]+[Fe^t]\} \leq [Br^-] \leq 3.5\{[Cu^t]+[Fe^t]\} \quad (14)$$

provided that in the foregoing formulae (1) through (14), $[Cu^t]$, $[Br^-]$, $[A^t]$ and $[Fe^t]$ respectively denotes the total ion concentration in liter of the aqueous medium;

$[Cu^t]$ being the total ion concentration (gram-atom/liter) of ionized copper ($Cu^+$ and $Cu^{++}$), $[Br^-]$ being the total ion concentration (gram-atom/liter) of the bromide ion ($Br^-$) which can solubilize copper and/or iron, $[A^t]$ being the total ion concentration (gram-ionic equivalent/liter) of the anion which at least includes a bromine ion and can solubilize copper and/or iron, all calculated as converted to monovalent anion, and

[Fe$^t$] being the total ion concentration (gram-atom/liter) of ionized iron (Fe$^{++}$ and Fe$^{+++}$).

Hereinafter the invention will be explained in further details.

According to the invention, an aliphatic olefin with 2–4 carbon atoms, preferably an aliphatic monoolefin, is contacted with an aqueous medium containing
 i. at least one cation selected from the group consisting of copper and iron ions, and
 ii. an anion which at least includes a bromine ion and can solubilize copper and/or iron, at 100°–200° C.

The aqueous medium to be employed in this invention, therefore, must contain either
 I. as the cation at least a copper ion, or
 II. as the cation at least an iron ion, or
 III. as the cation both copper and iron ions.

In other words, the aqueous medium to be employed in this invention may contain, optionally as dissolved therein, an element or elements other than copper or iron such as alkali metals, e.g., sodium, potassium and lithium; alkaline earth metals such as calcium, magnesium and barium; aluminium, cobalt, nickel, and zinc, but the medium must contain as the cation at least either one of copper and iron ions.

Again the aqueous medium to be employed in this invention must contain, besides the cation,
 ii. an anion which at least includes a bromine ion and can solubilize copper and/or iron. Therefore, the anion
 ii-a. may consist solely of a bromine ion which can solubilize copper and/or iron, or
 ii-b. may be an ionic mixture of the bromine ion of (ii-a) above and anion or anions other than the bromine ion; which can solubilize copper and/or iron.

Thus, an essential requirement for the anionic component is that it contains the bromine ion of (ii-a) in all cases.

It should be noted that, when the bromine ion is added to the aqueous medium of this invention in the form of a metal salt, typically a bromide of an alkali metal or alkaline earth metal such as potassium bromide, lithium bromide, calcium bromide or magnesium bromide; or when an anion or anions other than a bromine ion which essentially is capable of solubilizing copper and/or iron, such as the halogen ions other than bromine ion, e.g., chlorine, iodine and fluorine ions; or, for example, sulfate ion (SO$_4$=), sulfite ion (SO$_3$=), nitrate ion (NO$_3$$^-$), nitrite ion (NO$_2$$^-$), borate ion (BO$_3$ ≡ ), phosphate ion (PO$_4$ ≡ ) and phosphite ion (PO$_3$ ≡ ); are added to the aqueous medium similarly in the form of a metal salt or salts, for example, those of alkali metals or alkaline earth metals; such bromine ion or the anions other than the bromine ion released from such metal salts as the salts are dissolved in the aqueous medium, do not act as "the anion or anions which can solubilize copper and/or iron". Therefore, the aqueous medium to be employed in this invention must contain the anionic component essentially comprising a bromine ion which truly possesses the ability to solubilize copper and/or iron, excluding the anions added as counter ion of the metal or metals other than copper and/or iron.

As the anions other than a bromine ion which can solubilize copper and/or iron and therefore can be used in this invention, besides the above-mentioned halogen ions other than bromine ion and mineral acid ions such as those of sulfuric acid, boric acid, phosphoric acid and nitric acid, such organic acid ions as those of acetic acid, propionic acid and halogenoacetic acid may be used. However, when the concentration of such an organic acid ion in the aqueous medium becomes excessively high, a part of the glycol may be obtained in the form of an ester of the organic acid. Therefore, it is recommended that the concentration of such organic acid ion is kept below 25% by weight of the aqueous medium, preferably below 20% by weight.

The [Br$^-$] in the already defined formulae (2), (4), (6), (8), (12) and (14) denotes the total ionic concentration (gram-atom/liter) of the bromine ion having the ability to solubilize copper and/or iron, per one liter of the aqueous medium of the invention. Also the [A$^t$] in the formulae (3), (7) and (13) denotes the total concentration (gram-ionic equivalent/liter) of all the anions having the ability to solubilize copper and/or iron including a bromine ion, which are contained in one liter of the aqueous medium, when all the anions are calculated as converted to monovalent anions. An example of calculating the total concentration of the anions (gram-ionic equivalent/liter) by converting all the anions to monovalent anions may be given as follows.

For example, when the concentration of an n-valent anion is X (gram-atom/liter), the ionic equivalent concentration Y of the same anion (gram-ionic equivalent/liter) can be expressed by the equation below:

$$nX = Y$$

Consequently, when the aqueous medium of this invention contains, as the anions capable of solubilizing copper and/or iron, for example, 0.5 gram-atom/liter of monovalent ($n$=1) bromine ion (Br$^-$), 0.4 gram-atom/liter of monovalent acetate ion (CH$_3$COO$^-$), 0.3 gram-atom/liter of divalent ($n$=2) sulfate ion (SO$_4$=) and 0.2 gram-atom/liter of trivalent ($n$=3) phosphate ion (PO$_4$ ≡ ), the total concentration [A$^t$] of the anions all converted to monovalent anions (gram-ionic equivalent/liter) can be calculated as follows:

$$[A^t] = 1 \times 0.5 + 1 \times 0.4 + 2 \times 0.3 + 3 \times 0.2 = 2.1.$$

Also the [Cu$^t$] in the foregoing formulae (1), (3), (4), (9), (10), (13) and (14) denotes the total ionic concentration (gram-atom/liter) of the monovalent and divalent copper ions (Cu$^+$ and Cu$^{++}$) contained in one liter of the aqueous medium. Similarly, the [Fe$^t$] in the formulae (5), (7), (8), (9), (11), (13) and (14) denotes the total ionic concentration (gram-atom/liter) of the divalent and trivalent iron ions (Fe$^{++}$ and Fe$^{+++}$) contained in one liter of the aqueous medium.

Hereinafter the bromine ion which can solubilize the copper and/or iron will be conveniently referred to as the "effective bromine ion" and the anions other than bromine ion which can solubilize copper and/or iron, as "other effective anions", the two being collectively referred to as the "effective anions".

According to the invention, depending on the type of the cation contained in the aqueous medium (copper ion and/or iron ion), the concentrations of the cation and the effective anion, and the ratio therebetween, are controlled to be within the ranges specified by the already given formulae (1) through (14), and whereby the glycols corresponding to the starting olefins can be prepared at high production rate and at high yields.

Thus in the present invention,

I. when the cation in the aqueous medium is a copper ion, the concentrations of the copper ion and of effective anions, and the ratio of the two concentrations in the aqueous medium are controlled to satisfy the following formulae (1), (2), (3) and (4)

$$0.4 \leq [Cu^t] \leq 2.5 \quad (1)$$

$$0.8 \leq [Br^-] \leq 4.0 \quad (2)$$

$$1.75 [Cu^t] \leq [A^t] \leq 2.0 [Cu^t] \quad (3)$$

$$0.8 [Cu^t] \leq [Br^-] \leq 1.95 [Cu^t] \quad (4)$$

In that case, if the effective anion consists solely of effective bromine ion, the above formulae (3) and (4) are combined. Therefore, the formula (4') below must be satisfied:

$$1.75 [Cu^t] \leq [Br^-] \leq 1.95 [Cu^t] \quad (4')$$

Subtracting the formula (4) from formula (3), the formulae (3') and (3'') are derived:

$$0.95 [Cu^t] \leq [A^t] - [Br^-] \quad (3')$$

and $$[A^t] - [Br^-] \leq 0.05 [Cu^t] \quad (3'').$$

The above formula (3') signifies that, when the other effective anions are present in the aqueous medium at the minimum concentration of 0.95 [Cu$^t$] gram-atom/liter, the minimum concentration of the effective bromine anions in the same aqueous medium sufficient for the purpose is 0.8 [Cu$^t$] gram-atom/liter. Also the formula (3'') signifies that, when effective bromine ion is present in the aqueous medium at the maximum concentration of 1.95 [Cu$^t$] gram-atom/liter, the maximum allowable concentration of other effective anions in the same medium is 0.05 [Cu$^t$] gram-atom/liter.

Again, if the effective bromine ion concentration is, for example, at the minimum value of 0.8 [Cu$^t$] gram-atom/liter, the allowable concentration of other effective anions ranges from 0.95 [Cu$^t$] to 1.2 [Cu$^t$] gram-atom/liter.

According to the invention, furthermore, it is preferred to control the ionic concentrations and the ratio therebetween in the aqueous medium so that at least one of the formulae (1), (2), (3) and (4) should satisfy at least one of the formulae (1a), (2a), (3a) and (4a) below:

$$0.6 \leq [Cu^t] \leq 1.6 \quad (1a)$$

$$0.9 \leq [Br^-] \leq 3.0 \quad (2a)$$

$$1.8 [Cu^t] \leq [A^t] \leq 1.95 [Cu^t] \quad (3a)$$

$$1.2 [Cu^t] \leq [Br^-] \leq 1.9 [Cu^t] \quad (4a)$$

Similarly to the formulae (3) and (4), the above formulae (3a) and (4a) mean that, when effective bromine ion alone is present in the aqueous medium, the formula (4a') below must be satisfied:

$$1.8 [Cu^t] \leq [Br^-] \leq 1.9 [Cu^t] \quad (4a')$$

According to our studies, in the preparation of a glycol corresponding to the starting olefin by contacting the olefin with an aqueous medium containing copper ion as the cation, the formation rate of glycol is reduced if the ratio of effective bromine ion concentration [Br$^-$] to the copper ion concentration [Cu$^t$] is less than the minimum value defined by the foregoing formula (4), preferably (4a); and if the ratio exceeds the upper limit, formation rate of side-product increases to lower the selectivity for the glycol, both cases being objectionable for the purpose of this invention.

Compared with the effective bromine ion, however, other effective anion has somewhat less influence on the side-reaction, and therefore can be added in slight excess of the maximum allowable concentration of effective bromine ion, so far as the ratio of concentrations specified by the formula (3), preferably the formula (3a), is not deviated.

Also according to the invention, if

II. the cation present in the aqueous medium is an iron ion, the respective concentrations of the iron ion and effective anion and the ratio therebetween must be controlled to satisfy the formulae below:

$$0.3 \leq [Fe^t] \leq 2.0 \quad (5)$$

$$0.5 \leq [Br^t] \leq 6.0 \quad (6)$$

$$2.0 [Fe^t] \leq [A^t] \leq 3.0 [Fe^t] + 4.0 \quad (7)$$

$$1.0 [Fe^t] \leq [Br^-] \leq 3.0 [Fe^t] + 1.0 \quad (8)$$

In the glycol-forming reaction according to the present invention, favorable glycol-forming rate can be obtained at lower side of concentration range of iron ions [Fe$^t$] compared with the case of copper ions [formula (5)]. On the other hand, as shown by the formulae (7) and (8), the allowable range of concentration ratio of effective anion [A$^t$] or [Br$^-$] to iron ion [Fe$^t$] is broader than the case of copper ions, equally giving high glycol-forming rate and high glycol selectivity.

Also, as will be described later, when iron ions are used as the catalyst, equally high glycol-forming rate and the selectivity as obtainable with the use of copper ions can be achieved at lower reaction temperature. Furthermore, iron ions have such advantages over copper ions that they are cheaper, has less corrosive property and less tendency of environmental pollution.

Incidentally, the above formulae (7) and (8) mean that, similarly to the formulae (3) and (4) defining the case of copper ion, when the effective anion in the aqueous medium consists substantially of a bromine ion only, the formula (8') below formed by combining the formulae (7) and (8) must be satisfied.

$$2.0 [Fe^t] \leq [Br^-] \leq 3.0 [Fe^t] + 1.0 \quad (8')$$

The above statement is applicable also to the formulae (7a) and (8a), as well as to (7b) and (8b) below:

In the present invention, it is preferred that at least one of the conditions defined by the formulae (5) through (8) is controlled to satisfy at least one of the formulae (5a) through (8a) below.

$$0.4 \leq [Fe^t] \leq 1.5 \quad (5a)$$

$$0.7 \leq [Br^-] \leq 4.0 \quad (6a)$$

$$2.1 [Fe^t] \leq [A^t] \leq 3.0 [Fe^t] + 3.0 \quad (7a)$$

$$1.0 [Fe^t] \leq [Br^-] \leq 3.0 [Fe^t] + 0.5 \quad (8a)$$

It is particularly preferred that, furthermore, at least one of the formulae (5b) through (8b) below should be satisfied:

$$0.5 \leq [Fe^t] \leq 1.2 \qquad (5b)$$

$$1.0 \leq [Br^-] \leq 3.0 \qquad (6b)$$

$$2.2 [Fe^t] \leq [A^t] \leq 3.0 [Fe^t] + 2.0 \qquad (7b)$$

$$1.2 [Fe^t] \leq [Br^-] \leq 3.0 [Fe^t] \qquad (8b)$$

Those formulae, particularly the sets of formulae (7) and (8); (7a) and (8a); and (7b) and (8b), signify the very same relations described as to the case of copper ions used as the cation.

Furthermore if,

III. the cation in the aqueous medium consists of copper and iron ions, the concentrations of the cation and of the effective anions, and the ratio therebetween should be controlled to satisfy the conditions defined by the formulae (9)–(14) below, to achieve both high formation rate of glycol and high glycol selectivity:

$$0.05 \leq [Cu^t] + [Fe^t] \leq 1.6 \qquad (9)$$

$$0.01 \leq [Cu^t] \qquad (10)$$

$$0.01 \leq [Fe^t] \qquad (11)$$

$$0.5 \leq [Br^-] \leq 4.0 \qquad (12)$$

$$2.0\{[Cu^t]+[Fe^t]\} \leq [A^t] \leq 3.5\{[Cu^t]+[Fe^t]\}+4.0 \qquad (13)$$

$$1.0\{[Cu^t]+[Fe^t]\} \leq [Br^-] \leq 3.5\{[Cu^t]+[Fe^t]\} \qquad (14)$$

One great advantage of using the copper ions and iron ions in combination as the catalyst for the reaction intended by the invention is that, their use even at low concentrations in the aqueous medium can achieve far greater formation rate of glycol compared with that achieved above with either copper ions or iron ions alone, such as twice to four times, with substantially equivalent selectivity of glycol.

When the effective anion in the aqueous medium consists substantially of effective bromine ion alone, the formulae (13) and (14) are combined, similarly to the cases of formulae (3) and (4), or (7) and (8), into the formula (14') below:

$$2.0\{[Cu^t]+[Fe^t]\} \leq [Br^-] \leq 3.5\{[Cu^t]+[Fe^t]\} \qquad (14')$$

which must be satisfied by the composition of the aqueous medium. This statement also applies to the later appearing formulae (13a) and (14a), or (13b) and (14b).

Again, when the combination of copper ions and iron ions is used as the cation of the catalyst, it is preferred to control the conditions defined by the foregoing formulae to also satisfy the formulae (9a) through (14a) below:

$$0.2 \leq [Cu^t] + [Fe^t] \leq 1.4 \qquad (9a)$$

$$0.05 \leq [Cu^t] \leq 0.8 \qquad (10a)$$

$$0.2 \leq [Fe^t] \qquad (11a)$$

$$0.5 \leq [Br^-] \leq 3.5 \qquad (11a)$$

$$2.05\{[Cu^t]+[Fe^t]\} \leq [A^t] \leq 3.5\{[Cu^t]+[Fe^t]\}+2.5 \qquad (13a)$$

$$1.1\{[Cu^t]+[Fe^t]\} \leq [Br^-] \leq 3.2\{[Cu^t]+[Fe^t]\} \qquad (14a)$$

It is particularly advantageous, furthermore, to control the conditions to satisfy the formulae (9b) through (14b) below:

$$0.4 \leq [Cu^t] + [Fe^t] \leq 1.2 \qquad (9b)$$

$$0.10 \leq [Cu^t] \leq 0.4 \qquad (10b)$$

$$0.4 \leq [Fe^t] \qquad (11b)$$

$$1.0 \leq [Br^-] \leq 3.0 \qquad (12b)$$

$$2.10\{[Cu^t]+[Fe^t]\} \leq [A^t] \leq 3.5\{[Cu^t]+[Fe^t]\}+1.5 \qquad (13b)$$

$$1.2\{[Cu^t]+[Fe^t]\} \leq [Br^-] \leq 3.0\{[Cu^t]+[Fe^t]\} \qquad (14b)$$

In case the copper ions and iron ions are used in combination as the catalyst as above, it is preferred that the iron ion concentration in the aqueous medium should be at least equivalent to, or higher than, the copper ion concentration.

As in the above, according to the invention it is possible to make glycol from the corresponding olefin, at very high production rate and high selectivity, by using the combination of copper ions and iron ions as the catalyst, even at very low concentrations.

Incidentally, as to the foregoing formulae (9) through (14), particularly as to the formulae (13) and (14), (13a) and (14a), and (13b) and (14b), quite similar relations to those described as to the use of copper ions alone exist.

[Reaction of the Invention]

According to the invention, the starting olefin is contacted with the aqueous medium in which the concentrations of cations (copper ions and/or iron ions) and effective anions, and the ratio therebetween are adjusted to satisfy the conditions defined by the formulae (1) through (14), and thereby a glycol corresponding to the olefin can be produced. In that practice, either by effecting the contact in the presence of molecular oxygen or by contacting at least a part of the reaction mixture obtained by the first reaction with molecular oxygen in a system same or different from the first reaction system, the inactivated, low valent copper ion and/or iron ion having served as the catalyst can be regenerated to the high valent, active ion.

Therefore, according to the invention it is preferred to effect the contact of the aliphatic olefin with the aqueous medium in the presence of molecular oxygen, or to contact the glycol-containing reaction mixture obtained upon contacting the aliphatic olefin with the aqueous medium, with molecular oxygen in the same or different vessel from that in which the first reaction is performed.

It is preferred in this invention to contact at least a part of the glycol-containing reaction mixture obtained by contacting the aliphatic olefin with the aqueous medium, with molecular oxygen in a vessel different from that in which the first contact is effected, and to recycle at least a part of the reaction mixture contacted with the molecular oxygen to the first contacting system of the olefin with the aqueous medium. This preferred embodiment makes it possible to safely run the glycol-forming reaction avoiding the direct contact of olefin with molecular oxygen at such high temperatures as 100°–200° C., while regenerating the catalyst to allow continuous preparation of glycol from the olefin.

The main reactions of the invention can be expressed theoretically by the formulae below, taking the simplest form of olefin, i.e., ethylene, for example. While the following explanations are given mainly as to the case of using ethylene as the olefin, they are perfectly applicable to the cases using other olefins such as propylene or butene.

i. Oxidation of olefin (reaction of olefin with catalyst)

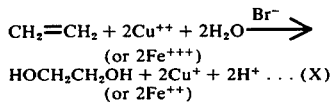

ii. Regeneration of catalyst (reaction of catalyst with $O_2$)

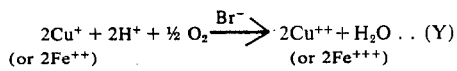

The above reactions (X) and (Y) progress simultaneously when the olefin and molecular oxygen are simultaneously catalytically reacted in the presence of the catalyst (single-stage process), but the two advance separately when the olefin and molecular oxygen are separately contacted with the catalyst (two-stage process). In either case, as the result of the two reactions taking place, the total reaction can be expressed as follows:

iii. Total reaction [reaction (X) + reaction (Y)]

Thus in appearance, in the main reaction of the invention the copper ions, iron ions, bromine ion and other anions exhibit simply the catalytic action for the above total reaction, but in essence the main reaction is the combination of two independently progressing, stoichiometric reactions, one being that between the copper and/or iron ion with olefin, and the other, said ion or ions with molecular oxygen.

The reaction (Y) very easily progresses under the specified conditions of the present invention because the $H^+$ supply is abundant, and the metal ions are regenerated to their high valent state. Under the conditions deviated from the specified ranges according to the invention, however, the rate of regeneration is drastically reduced when $H^+$ supply becomes insufficient, and occasionally the low valent metal ions accumulate in the liquid. If the reaction (Y) is excessively promoted in that state by such means as raising the partial pressure of oxygen in the reaction system, such side-products as copper oxy-bromide [$CuBr_2.3Cu(OH)_2$] and/or iron oxide ($Fe_2O_3$) and iron hydroxide [$Fe(OH)_3$] which are insoluble in the reaction liquid are formed and precipitated out of the system, never to again participate in the oxidation reaction of olefin as they are.

It is not yet entirely clear in what forms the bromine ion, copper ions and/or iron ions are present in the reaction system according to the invention, and in what forms they participate in the reaction, but presumably the reactions progress by suitable linking or coordination of $Br^-$ ion with $Cu^{++}$, $Cu^+$, $Fe^{+++}$ and $Fe^{++}$.

[Reactants and the preparations for reaction conditions]

The copper and iron ions to be employed in the invention can be obtained by dissolving optional copper salt and iron salt in the reaction system.

The types of such copper salts and iron salts are not critical, so far as they are soluble in the reaction medium composed chiefly of water, under the specified reaction conditions. Under the reaction conditions, those salts are presumed to form copper ions, iron ions, or their complex ions, and to participate in the reaction.

Therefore, the copper salts and iron salts employed in the invention are deemed to be effective to the reaction, so long as they are dissolved in the reaction medium composed chiefly of water. As the useful salts, for example, halides, inorganic acid salts and organic acid salts of copper and iron, e.g., bromides, chlorides, sulfates, borates, phosphates, nitrates and acetates may be named.

As already mentioned, the components which participate in the reaction of this invention as so-called catalyst are no other than copper, iron, and bromine ions, all other many anions and cations not directly participating in the reaction. Therefore, the most preferred form of the copper and iron salts to be used in the subject process is the bromide such as copper bromide ($CuBr_2$, $CuBr$) and iron bromide ($FeBr_3$, $FeBr_2$), double salt thereof (e.g., copper oxybromide such as $CuBr_2.3Cu(OH)_2$) or complex salt.

The copper or iron salt which is insoluble in the reaction medium chiefly composed of water (for example, hydroxide, oxide or carbonate) in ineffective to the reaction as it is. Therefore, such a salt shows no catalytic effect unless at least a part thereof can take the form of a soluble salt during the reaction (by the concurrent presence of, for example, a mineral acid, organic acid or the like). The presence of such insoluble salt, however, is not particularly detrimental to the reaction.

The effective bromine ion to be employed in the subject process is supplied to the reaction system by an optional bromine ion source. The source may be any, so far as it is capable of supplying bromine ion to the reaction system of this invention. For example, molecular bromine, hydrogen bromide, organobromine compounds (e.g., ethyl bromide, ethylene dibromide and propylene dibromide) and bromide of copper or iron can be suitably used.

It should be particularly noted that, if molecular bromine or hydrogen bromide is used, at least its presence in the reaction system during the reaction in the form of molecular bromine or a free acid must be avoided by all means; Particularly the presence of molecular bromine is entirely useless, even detrimental, to the reaction intended by this invention.

Again the presence of an excessively great amount of free hydrobromic acid markedly decreases the yield of glycol in the subject process.

When iron ions are present in the aqueous medium to be employed in the invention, however, hydrogen bromide may be used in the form of free acid within the aforesaid limitative condition on [$Br^-$], for particularly inhibiting inactivation of iron ions by precipitation or for promoting their regenerative reaction.

Organobromine compounds may be present in the reaction system of the subject process, on the premises that they generate bromine ion in the reaction system, before or during the reaction, by, for example, hydrolysis, and that the bromine ion so generated does not exceed the critical upper concentration specified in the subject process. Incidentally, the organobromine compound itself takes no part in the reaction as it is.

Bromides of alkali metals or alkaline earth metals as aforesaid cause the presence of such metal cations in the reaction system of the subject process, which form ion pairs with the bromine ion. Consequently the bromine ion substantially ceases to function as the effective bromine ion to participate in at least the reaction for making glycol from olefin. Therefore, for the effective utilization of the bromides of alkali metals or alkaline earth metals, either such metal cations are removed from the system before the reaction, or, the concurrent presence of, for example, a mineral acid is caused to make ion pairs of the mineral acid anions other than the bromine ion with the metal ions, leaving the effective bromine ion in the system at the desired concentration.

In any case, ions other than the copper ions, iron ions and bromine ion are essentially inert to the reaction of the subject process as aforesaid. Considering this fact, the most preferred bromine ion source to be employed in this invention is copper bromides, iron bromides, and double and complex salts thereof.

And, if during the reaction the bromine ion is lost from the system upon, for example, advance of a side-reaction, hydrogen bromide is the best for supplementing the shortage.

As is apparent from the foregoing reaction formulae (X) and (Y), bromine ion does not directly participate in the reaction of the subject process. If this fact alone is considered, the reason why the presence of effective bromine ion abnormally promotes the reaction as demonstrated in the later given experiments (Example and Control) is difficult to understand, particularly because the presence of chlorine ion as a similar halogen produces none of such effect. It is presumed, therefore, that in the course of progress of the reaction (X) and (Y), there may be a stage at which essentially the bromine ion directly participate in the reaction, but it is not yet entirely clear.

It is indeed surprising, in any case, that the olefin-oxidizing reaction (glycol-forming reaction) with copper salt and/or iron salt in an aqueous solution of relatively low catalyst concentration according to the subject process is markedly promoted by the presence of bromine ion, quite differently from the effect of chlorine ions' presence which also is a halogen.

Of the other ions which may be concurrently present in the reaction system of the subject process, for example, the anions such as $OH^-$, $I^-$, $S^=$ and $(COO)_2^-$ reduce or insolubilize copper salts and iron salts. Presence or $Cl^-$ is not detrimental to the subject process unless it is present in great amount, but derives no advantage. Ions of alkali metals or alkaline metals should be avoided, because they act to inactivate effective bromine ion as aforesaid. However, those other cations and anions could be advantageously used for adjusting pH of the reaction solution or for adjusting the activities of the reactants. In certain cases, therefore, it may be desirable to use the suitably controlled amount of such ion sources to cause the presence of such ions at the controlled quantities.

In the reaction system of the subject process, it is possible that the concentration of effective bromine ion varies during the reaction with the progress of the reaction, or depending on the types of ions present in the reaction system. This statement also applies to the copper salts and/or iron salts employed. [For example, they may form insoluble $FeO$, $Fe_2O_3$, $CuBr_2 \cdot 3Cu(OH)_2$, or side-product such as molecular bromine, alkylene bromide or alkyl bromide, or may produce common-ion effect].

Therefore, it is desirable in practicing the present invention that the types and quantities of copper salt and/or iron salt, bromine ion source and other additives, if used, should be so selected as to maintain the reaction-promoting ability of copper ions, iron ions and bromine ions at above a certain constant level during the reaction. The preferred compounds as the copper salt and/or iron salt and bromine ion source in common are cuprous bromide, cupric bromide, $CuBr \cdot 2CuBr_2$, ferrous bromide and ferric bromide.

The type of olefin to be employed in the subject process is not critical, but preferably the olefins with 2 to 4 carbon atoms, particularly 2 to 3 carbon atoms (ethylene and prepylene) are used. Generally, with the increase in carbon number of the olefin, yield of carbonyl compound as a side-product also increases.

The molecular oxygen to be employed in this invention may be purely the molecular oxygen, or air, or any gaseous matter obtained by diluting the foregoing with an inert gas. As is apparent also from the given reaction formula (X), the oxidation reaction of olefin itself essentially requires no molecular oxygen. Therefore the concurrent presence of molecular oxygen with the olefin is not always necessary. Again, as is apparent from the reaction formula (Y), the regenerative reaction of copper ions and/or iron ions is essentially independant from the oxidation reaction of the olefin. Accordingly, in this point also the constant concurrent presence of molecular oxygen with the olefin is unnecessary, and it is premissible to adopt two-stage reaction, i.e., for example the olefin alone is catalytically oxidized by the action of catalyst, and thereafter the copper ions and/or iron ions are regenerated. Furthermore, if the olefin and molecular oxygen are caused to be concurrently present, the molecular oxygen and/or olefin are preferably diluted with an inert gas.

The water to be employed in the subject process functions as the reaction medium as well as one of the reactants. The preferred pH of the reaction medium is 7–0, particularly 5–0.5, inter alia, 4–1. Also the glycol as the reaction product and the side-produced derivatives thereof can be used together with water. In order for improving the solubility of copper salt and/or iron salt as well as for activating bromine ion, an acid such as $H_2SO_4$, $HNO_3$, $HCl$ or $CH_3COOH$, or a salt thereof may be added to the reaction system within the critical conditions specified in this specification. Likewise, various organic liquids, solubilizing agent, surfactant and the like may be added in suitable amounts for adjusting the solubilities of the reactants, reaction product and side products in reaction system. However, the subject process essentially requires none of such additives other than the reactants. Presence of an excessive amount of an organic acid (for example, acetic acid or propionic acid) in the reaction system is objectionable, because the formed glycol tends to form an ester of said acid. In order for promoting the oxidative regeneration of copper ions and/or iron ions, if necessary such oxidizing agent as nitric acid, perhalogenoacid, molecular halogen, hydrogen peroxide or ozone may be used concurrently with molecular oxygen, or electrolytic oxidation may be applied.

However, normally the reaction of this invention requires no such oxidizing agent other than molecular oxygen, and the concurrent use of such oxidizing agent may not necessarily lead to more advantageous progress of the reaction according to the subject process.

The reaction of the invention may be performed in the atmosphere of an inert gas not directly participating in the reaction, such as nitrogen, argon or carbon dioxide. Hydrocarbons such as methane, ethane and the like may be concurrently present in the atmosphere.

The reaction progresses under atmospheric pressure, but in order to promote its progress, it is desirable to employ an elevated pressure. The reaction pressure is not critical, but for practical purposes the total pressure of 5–200 $Kg/cm^2$, preferably 10–60 $Kg/cm^2$, olefin partial pressure of 1–50 $Kg/cm^2$, and oxygen partial pressure of 1–10 $Kg/cm^2$, are employed. The progress of the reaction is proportionate to the partial pressure of olefin and oxygen to a certain degree, but in practice the higher partial pressures are not necessarily advantageous.

The reaction temperature may range 100°–200° C., preferably 140°–180° C. when the aqueous medium of the invention contains as the cation copper ions, or copper ions and iron ions. It is preferably 120°–180° C. when the medium contains iron ions as the cation. With the rise in reaction temperature the reaction progresses at a greater rate, but at an excessively high temperature the side reaction or secondary reactions of the product is apt to take place to lower the yield of glycol.

Also when the reaction of the subject process is practiced by the afore-described two-stage procedure, the regenerative reaction of copper ions and/or iron ions requires none of such particularly high temperature. Therefore, optional temperature above room temperature may be employed.

Furthermore, a practical advantage is found with the present invention that, by controlling the ratio of concentrations among the copper ions and/or iron ions and bromine ion within the specified ranges, as a side-effect the corrosion of the reactor can be markedly reduced. This effect is particularly conspicuous when iron ions are used singly or together with copper ions.

Hereinafter the invention will be explained more specifically with reference to the working Examples, in which [ ] denotes the concentration (gram-atom/liter), unless otherwise specified, and partial pressures of ethylene and oxygen are shown by the unit of $Kg/cm^2$. The determination of ethylene glycol was performed by gas chromatography (aqueous solution) and oxidation with periodic acid. The determination of other compounds was performed mainly by gas chromatography, and if necessary chemical analysis method was concurrently employed.

EXAMPLES 1–3 AND CONTROLS 1–4

Mixed aqueous solutions of $CuBr_2$ and $CuBr$ of various concentrations as specified in Table 1 were prepared, and a predetermined, fixed amount of each of the solution was put in an autoclave accommodating a stirrer, and heated to 140° C. After the subsequent ethylene supply to a pressure of 10 $Kg/cm^2$, the autoclave was sealed, and the content was reacted for a predetermined period under stirring. The rate of ethylene formation in each run was as shown in Table 1.

Table 1

|  |  | $CuBr_2$ Concentration (mol/liter) | $CuBr$ Concentration (mol/liter) | $Cu^{++}/Cu^+$ (g-ion ratio) | $[Br^-]/[Cu^+]$ (g-ion ratio) | EG Production Rate (mol/l hr.) |
|---|---|---|---|---|---|---|
| Example | 1 | 0.80 | 0.20 | 8.0/2.0 | 1.80 | 0.22 |
| "  | 2 | 0.80 | 0.10 | 8.9/1.1 | 1.89 | 0.53 |
| "  | 3 | 0.80 | 0.05 | 9.4/0.6 | 1.94 | 0.65 |
| Control | 1 | 0.80 | 0.80 | 5.0/5.0 | 1.50 | 0.14 |
| "  | 2 | 0.80 | 0.50 | &.2/3.8 | 1.62 | 0.14 |
| "  | 3 | 0.80 | 0.40 | 6.7/3.3 | 1.67 | 0.14 |
| "  | 4 | 0.80 | 0.30 | 7.3/2.7 | 1.73 | 0.17 |

EXAMPLES 4–12 AND CONTROLS 5–10

An autoclave with titanium lining equipped with a high-speed rotatory agitator, gas inlet pipe and gas outlet pipe was charged with an aqueous solution of $CuBr_2$, $CuBr$, and HBr at various concentrations, heated to 160° C., and through which a pressurized ethylene-oxygen-nitrogen gaseous mixture was passed (ethylene partial pressure = 8.9 $Kg/cm^2$, oxygen partial pressure = $Kg/cm^2$), and reacted under violent agitation.

The low boiling side-products formed during the reaction were distilled off from the system as entrained by the outgoing gaseous flow, which were caught by a low-temperature trap. Other products were refluxed into the system by the action of the condenser provided at the exit of the gas so as to prevent their escape from the system.

The composition in the autoclave was occasionally sampled and analyzed. At approximately 20 minutes after the reaction started, the composition of the reactants in the reaction system became stationary. The compositions of the reaction liquids at that time and the results of the reaction were as shown in Table 2.

In the Controls wherein $[Br^-]/[Cu^t]$ was greater than 2.0, HBr was intermittently supplied into the reaction system to maintain the high $[Br^-]/[Cu^t]$ value, the HBr concentration given in Table 2 being the average value.

Table 2

| | | Composition of Reaction Liquid | | | | Results of Reaction Ethylene Glycol(EG) | | |
|---|---|---|---|---|---|---|---|---|
| | | [Cu'] | [Cu++] | [Cu+] | [Br-] | [Br-]/[Cu'] | Production Rate (mol/l.hr.) | Yield (mol %) | Remarks |
| Control | 5 | 0.215 | 0.210 | 0.005 | 0.424 | 1.972 | 0.302 | 78.9 | EG production rate was too low for practical purposes |
| Example | 4 | 0.658 | 0.650 | 0.047 | 1.280 | 1.945 | 1.250 | 78.3 | |
| " | 5 | 0.799 | 0.700 | 0.098 | 1.498 | 1.875 | 1.922 | 87.8 | |
| " | 6 | 0.985 | 0.826 | 0.158 | 1.812 | 1.840 | 1.842 | 81.3 | |
| " | 7 | 0.963 | 0.877 | 0.086 | 1.846 | 1.917 | 1.808 | 80.9 | |
| " | 8 | 1.165 | 0.972 | 0.193 | 2.137 | 1.834 | 2.492 | 79.6 | |
| " | 9 | 1.373 | 1.123 | 0.248 | 2.490 | 1.814 | 2.889 | 75.9 | |
| " | 10 | 1.452 | 1.102 | 0.350 | 2.559 | 1.792 | 3.129 | 73.1 | |
| " | 11 | 1.691 | 1.514 | 0.180 | 3.205 | 1.895 | 2.789 | 70.1 | |
| " | 12 | 1.735 | 1.513 | 0.212 | 3.306 | 1.902 | 3.026 | 70.5 | |
| Control | 6 | 1.319 | free HBr(*) | | 0.579 | 3.218 | 2.439 | 2.410 | 38.5 | In all cases formation of large amount of ethylene dibromide was observed. |
| " | 7 | 1.459 | free HBr | | 0.270 | 3.188 | 2.185 | 2.896 | 48.0 | |
| " | 8 | 1.475 | free HBr | | 0.150 | 3.099 | 2.101 | 2.838 | 51.5 | |
| " | 9 | 1.606 | free HBr | | 0.103 | 3.315 | 2.064 | 2.976 | 55.2 | |
| " | 10 | 2.532 | 2.202 | 0.330 | 4.738 | 1.871 | 2.255 | 41.0 | EG yield was too low for practical purposes. |

In the run marked with *, HBr was added instead of CuBr.

EXAMPLE 13–20 AND CONTROL 11

The reactor similar to that used in Examples 4–12 was charged with copper bromide ($CuBr_2$, $CuBr$) of various concentration, and heated from outside. Into the reactor an ethylene-oxygen mixed gas at various mixing ratio was fed under an elevated pressure to effect the reaction with violent agitation, similarly to Examples 4–12.

The reaction conditions and the results thereof were as shown in Table 3.

Table 3

| | | Composition of Reaction Liquid | | | Reaction Pressure (partial pressure) $PC_2H_4$, $PO_2$ (Kg/cm²) | Reaction Temp. (° C.) | Results of Reaction Ethylene Glycol | |
|---|---|---|---|---|---|---|---|---|
| | | [Cu'] | [Br-] | [Br-]/[Cu'] | | | Production Rate (mol/l.hr.) | Yield (mol %) |
| Control | 11 | 0.991 | 1.708 | 1.724 | 9.2, 3.9 | 140 | 0.844 | 63.2 |
| Example | 13 | 1.010 | 1.941 | 1.922 | 7.8, 3.3 | 180 | 3.285 | 70.4 |
| " | 14 | 1.075 | 1.995 | 1.855 | 0.9, 0.9 | 160 | 1.088 | 74.5 |
| " | 15 | 1.084 | 2.057 | 1.898 | 1.1, 3.7 | 160 | 1.604 | 80.7 |
| " | 16 | 1.051 | 1.919 | 1.826 | 3.8, 1.0 | 160 | 1.750 | 77.6 |
| " | 17 | 1.005 | 1.775 | 1.766 | 3.6, 3.6 | 160 | 1.905 | 79.5 |
| " | 18 | 0.923 | 1.685 | 1.826 | 10.3, 5.6 | 160 | 3.064 | 83.6 |
| " | 19 | 1.070 | 1.920 | 1.794 | 19.7, 3.6 | 160 | 2.703 | 82.8 |
| " | 20 | 0.898 | 1.681 | 1.871 | 28.4, 3.6 | 160 | 1.905 | 79.5 |

Table 4

| Reaction Conditions and Results | Run No. | Control 12 | Control 13 | Control 14 |
|---|---|---|---|---|
| Concentration of $CuCl_2$ aqueous solution (mol/l) | | 1.0 | 2.0 | 3.0 |
| Ethylene Conversion (mol %) | | 0.64 | 0.98 | 1.59 |
| Formed Ethylene Glycol (mol/l) | | 0.050 | 0.046* | 0.052 |
| Ethylene Glycol Yield (mol%) | | 78.1 | 46.9 | 32.7 |

CONTROLS 12–14

The reactor similar to that used in Examples 4–12 was charged with an aqueous solution of $CuCl_2$ of the concentration indicated in Table 4, and heated to 160° C. Through the reactor then a gaseous mixture of ethylene and air (ethylene partial pressure, 16 Kg/cm²; oxygen partial pressure, 2 Kg/cm²) was passed and reacted for an hour under violent agitation. The results of the reaction were as given in Table 4.

Incidentally, the composition of the reactants in the system was substantially constant throughout the reaction.

Note* In the run mared with *, besides the ethylene glycol 0.004 mol/liter of ethylene vchlorohydrin and 0.038 mol/liter of ethylene dibromide were formed.

From the results shown in Tables 2, 3 and 4, it can be understood that, compared with the use of chlorine as a halogen, bromine produces 10 to 60 times greater amount of ethylene glycol.

EXAMPLE 21

A $FeBr_3$ aqueous solution of the concentration 1.14 mol/liter was poured into the same autoclave as used in Examples 1–3, and heated to 140° C. Into the autoclave then ethylene was fed to a pressure of 30 Kg/cm², sealed and reacted under stirring.

After 1 hour's reaction the aqueous solution in the autoclave was analyzed to reveal that the trivalent iron ions in the liquid were completely consumed, and the corresponding amount of oxidation product of ethylene composed chiefly of ethylene glycol was formed.

In this Example, the oxidizing rate of ethylene by the iron ions was markedly greater than that by copper ions.

EXAMPLES 22–26 AND CONTROL 15

A reactor similar to that used in Examples 4–12 was charged with an aqueous solution of iron bromide ($FeBr_3$ and $FeBr_2$) of various concentration, or with hydrogen bromide (HBr), and heated externally to 160° C. Through the reactor a pressurized ethylene-oxygen-nitrogen gaseous mixture (ethylene partial pressure = 8.9 Kg/cm², oxygen partial pressure = 3.8 Kg/cm²) was passed at an excess, and reacted with violent stirring.

The low-boiling side-products (mainly trace of carbon dioxide and a minor amount of acetaldehyde) formed during the reaction was distilled off from the system as accompanied by the effluent gas, which were caught by a low-temperature trap or the like. The other products, however, were refluxed into the system by means of a condenser provided at the exit of the gas.

The content of the autoclave was extracted intermittently and analyzed. The reaction assumed the stationary state very quickly after the reaction started. The compositions of the reaction liquids determined at that state and the results of the reaction were as shown in Table 5.

CONTROLS 16–18

A reactor similar to that used in Examples 22–26 was charged with an aqueous solution of $FeCl_3$ at various concentrations as indicated in Table 6, and externally heated to 160° C. Through the reactor an ethylene-air gaseous mixture (ethylene partial pressure = 16 Kg/cm², oxygen partial pressure = 2 Kg/cm²) was passed and reacted for 2 hours with violent stirring. The composition of the reactants in the reaction system was substantially constant throughout the reaction period. The results of the reaction were as shown in Table 6.

Table 6

| Reaction Conditions and Results | Run | Control 16 | Control 17 | Control 18 |
|---|---|---|---|---|
| $FeCl_3$ Concentration of Aqueous Solution (mol/l) | | 1.0 | 2.0 | 5.0 |
| Ethylene Conversion (mol %) | | — | — | 0.57 |
| Formed Ethylene Glycol (mol/l) | | 0.012 | 0.019 | 0.021 |
| Ethylene Glycol Yield (mol %) | | Approx. 70 | — | 18.6 |

EXAMPLES 27–34 AND CONTROL 19

A reactor similar to that used in Examples 4–12 was charged with a mixed aqueous solution of copper bromide and iron bromide at various concentrations, and heated externally to 160° C. Through the reactor a pressurized ethylene-oxygen-nitrogen mixed gas (ethylene partial pressure = 8.9 Kg/cm², oxygen partial pressure = 3.8 Kg/cm²) was passed and reacted in the manner similar to Examples 4–12. The results were as shown in Table 7.

Table 5

| | | Composition of Reaction Liquid | | | | Results of Reaction Ethylene Glycol | | Remarks |
|---|---|---|---|---|---|---|---|---|
| | | [Fe$^t$] | [Fe$^{+++}$] | [Fe$^{++}$] | [Br$^-$] | [Br$^-$]/[Fe$^t$] | Reaction Rate (mol/l.hr.) | Yield (mol %) | |
| Control | 15 | 0.200 | 0.020 | 0.181 | 0.599 | 2.995 | 0.059 | 56.2 | |
| Example | 22 | 0.383 | 0.028 | 0.355 | 1.095 | 2.859 | 1.299 | 80.3 | |
| " | 23 | 0.503 | 0.016 | 0.487 | 1.920 | 3.0+0.411/[Fe$^t$] | 1.318 | 75.3 | Reaction Temp. 140° C. |
| " | 24 | 0.527 | 0.028 | 0.499 | 2.020 | 3.0+0.439/[Fe$^t$] | 0.462 | 53.9 | Reaction Pressure |
| " | 25 | 0.652 | 0.052 | 0.600 | 1.813 | 2.781 | 1.750 | 77.6 | PC$_2$H$_4$ 9.2, |
| " | 26 | 0.822 | 0.048 | 0.744 | 2.031 | 2.471 | 2.001 | 68.8 | Po$_2$ 3.9 |

Table 7

| | | Composition of Reaction Liquid | | | | Results of Reaction Ethylene Glycol Production | | Remarks Results of reactions under identical conditions except either copper bromide or iron bromide alone was used (production rate of ethylene glycol and [yield]) | |
|---|---|---|---|---|---|---|---|---|---|
| | | [Cu$^t$] | [Fe$^t$] | [Br$^-$] | (Δ) | Rate (mol/l.hr.) | Yield (mol %) | | |
| Example | 27 | 0.097 | 0.047 | 0.310 | (2.153) | 0.636 | 8.13 | Cu alone 0.151 | [81.5] |
| | | | | | | | | Fe alone 0.008 | [ – ] |
| " | 28 | 0.101 | 0.244 | 0.729 | (2.113) | 1.827 | 85.1 | Cu alone 0.151 | [81.5] |
| | | | | | | | | Fe alone 0.270 | [60.1] |
| " | 29 | 0.201 | 0.135 | 0.683 | (2.033) | 1.548 | 86.2 | Cu alone 0.302 | [78.7] |
| | | | | | | | | Fe alone 0.039 | [ – ] |
| " | 30 | 0.201 | 0.406 | 1.252 | (2.063) | 2.659 | 82.5 | Cu alone 0.302 | [78.9] |
| | | | | | | | | Fe alone 0.999 | [80.3] |
| " | 31 | 0.202 | 0.555 | 1.622 | (2.143) | 3.254 | 77.6 | Cu alone 0.302 | [78.7] |
| | | | | | | | | Fe alone 1.520 | [75.0] |
| " | 32 | 0.302 | 0.301 | 1.326 | (2.199) | 2.075 | 91.4 | Cu alone 0.420 | [79.6] |
| | | | | | | | | Fe alone 0.222 | [67.2] |
| " | 33 | 0.493 | 0.229 | 1.444 | (2.322) | 2.421 | 82.6 | Cu alone 0.780 | [83.7] |
| | | | | | | | | Fe alone 0.101 | [63.7] |
| " | 34 | 0.900 | 0.205 | 2.210 | (2.000) | 2.362 | 74.1 | Cu alone 1.874 | [80.0] |
| | | | | | | | | Fe alone 0.060 | [ – ] |

Table 7-continued

|  | Composition of Reaction Liquid | | | | Results of Reaction Ethylene Glycol | | Remarks Results of reactions under identical conditions except either copper bromide or iron bromide alone was used (production rate of ethylene glycol and [yield]) |
|  | | | | | Production Rate | Yield | |
|  | [Cu$^t$] | [Fe$^t$] | [Br$^-$] | (Δ) | (mol/l.hr.) | (mol %) | |
|---|---|---|---|---|---|---|---|
| Control 19 | 2.236 | 1.386 | 7.200 | (1.988) | 2.106 | 32.1 | |

(Δ): The numerical values in the parentheses denote [Br$^-$]/ [Cu$^t$]+[Fe$^t$] .

EXAMPLES 35 to 36

Those Examples show the experiments in which the reaction system contains, as the ions other than copper and/or ions and bromine ion, alkali metal ions.

NaBr (1.003 mol/liter) was added to the reaction solution as used in Example 9, and LiBr (0.980 mol/liter), to the reaction liquid of Example 26, each to the concentration specified in the parentheses, and reacted in the reactor and by the method similar to those employed in Examples 4–12. The production rate of ethylene glycol was, respectively, 2.777 mol/l.hr. and 2.046 mol/l.hr. The results thus prove that the presence of such alkali metal ions and the counter bromine ions as the iron pairs in the solution has substantially no effect on the ethylene glycol formation.

It may be noted, however, that in the Runs the ethylene glycol yield was somewhat lower than the case wherein none of such iron pairs was added, as, respectively, 67.4% and 59.5%.

EXAMPLES 37–40 AND CONTROLS 20–21

Those Examples show the experiments in which the reaction system contains other anions than bromine ion which can solubilize copper.

A mixed aqueous solution containing, at various concentrations, CuBr$_2$, CuBr and CuSO$_4$, Cu$_3$(BO$_3$)$_2$, [Cu(OH)$_2$+$_{H3}$BO$_3$] or CuCl$_2$, was poured in the reactor similar to that used in Examples 4–12, and reacted with an ethylene-oxygen-nitrogen mixed gas by the method employed in Examples 4–12. The compositions of reaction liquids at the steady state of the reaction and the results were as shown in Table 8.

Table 8

| | Composition of Reaction Liquid | | | | | | |
|---|---|---|---|---|---|---|---|
| | | | | | Type and Concentration of Other effective Anion [A$^t$] – [Br$^-$] | | |
| | [Cu$^t$] | [Cu$^{++}$] | [Cu$^+$] | [Br$^-$] | (g-ion eq./l) | [Br$^-$]/[Cu$^t$] | [A$^t$]/[Cu$^t$] |
| Example 37 | 1.282 | 1.137 | 0.145 | 1.676 | SO$_4$$^=$, 0.816 | 1.307 | 1.944 |
| " 38 | 1.668 | 1.579 | 0.089 | 1.735/SO$_4$$^=$, 1.590 | 1.040 | 1.993 | |
| " 39 | 1.155 | — | — | 1.449 | BO$_3$$^=$, 0.850 | 1.255 | 1.990 |
| " 40 | 1.070 | — | — | 1.648 | Cl$^-$, 0.485 | 1.540 | 1.993 |
| Control 20 | 1.363 | 0.053 | 0.888 | So$_4$$^=$, 1.891 | 0.652 | 2.039 | |
| " 21 | 2.787 | 2.699 | 0.088 | 1.751 | SO$_4$$^=$, 3.800 | 0.628 | 1.992 |

| | Results of Reaction Ethylene Glycol | | |
|---|---|---|---|
| | Production Rate (mol/l.hr.) | Yield (mol %) | Remarks |
| Example 37 | 1.823 | 85 | Both the production rate and yield were better than the results of the run wherein [Br$^-$]=[A$^t$]=1.690, [Br$^-$]/[Cu$^t$] = 1.900 to achieve Production Rate 1.750 mol/l.hr., Yield 81.3 mol % |
| " 38 | 2.385 | 86.0 | |
| " 39 | 1.791 | 82.3 | "—"mark means no measurement was made. |
| " 40 | 2.102 | 76.9 | |
| Control 20 | 0.754 | 85.0 | |
| " 21 | 1.204 | 86.5 | |

EXAMPLES 41–43 AND CONTROL 22

Those Examples show the experiments in which the reaction system contains the other anions than bromine ions, which can solubilize iron.

Iron oxide (Fe$_2$O$_3$) was dissolved in hydrogen bromide (HBr) and sulfuric acid (H$_2$SO$_4$) and/or acetic acid (CH$_3$COOH) and formed into aqueous solutions of various concentrations. Each of the solutions was reacted with an ethylene-oxygen-nitrogen mixed gas using the reactor and by the method similar to those employed in Examples 22–26.

The composition of the reaction liquid to the steady state of the reaction and the results of the reaction were as shown in Table 9.

Table 9

| | [Fe'] | [Fe$^{+++}$] | [Fe$^{++}$] | [Br$^-$] | Composition of Reaction Liquid Tyfe and Concentration of Other Anions [A']-[Br$^-$] (g-ion eq./l) | [Br$^-$]/[Fe'] | [A']/[Fe'] |
|---|---|---|---|---|---|---|---|
| Example 41 | 0.577 | 0.064 | 0.513 | 1.217 | CH$_3$COO$^-$ 3.970 | 2.109 | $3.0 + \frac{3.456}{[Fe']}$ |
| Example 42 | 0.700 | — | — | 0.915 | SO$_4^=$ 1.820 | 1.307 | $3.0 \frac{0.635}{[Fe']}$ |
| Example 43 | 0.701 | — | — | 1.416 | SO$_4^=$, 0.9-10 | | |
| | | | | | CH$_3$COO$^-$ 1.588 | 2.020 | $3.0 \frac{1.811}{[Fe']}$ |
| Control 22 | 0.697 | 0.640 | 0.057 | 0.773 | CH$_3$COO$^-$, 7.940 | 1.109 | $3.0 \frac{6.622}{[Fe']}$ |

| | Results of Reaction Ethylene Glycol | |
|---|---|---|
| | Production Rate (mol/l.hr.) | Yield (mol %) Remarks |
| Example 41 | 2.235 | 78.0[1]   [1] glycol acetate content: no more than 1% |
| Example 42 | 2.351 | 76.2   "—"mark means no measurement was made. |
| Example 43 | 2.683 | 80.9 |
| Control 22 | 1.622 | 67.3[2]   [2] glycol acetate content: 9.7% |

EXAMPLE 44

This Example shows an experiment of the reaction using the mixed aqueous solution of copper bromide and iron bromide as specified in Examples 27–34, in which acetate ions were caused to be present as the other anions which can solubilize copper and iron.

In the same reactor as used in Examples 27–34, a mixed aqueous solution, in which ionic concentrations were respectively as follows:

[Cu'] = 0.150 g-atom/l

[Fe'] = 0.614 g-atom/l

[Br$^-$] = 1.613

([Br$^-$]/{[Cu'] + [Fe']} = 2.111

[CH$_3$COO$^-$] = 2.382 g-atom/l $([A']/ \{[Cu'] + [Fe']\} = 3.5 + \frac{1.321}{\{[Cu']+[Fe']\}}$ was reacted with an ethylene-oxygen-nitrogen gaseous mixture. The production rate of ethylene glycol was 3.526 mol/l.hr., and the yield was 78.9 mol %.

EXAMPLE 45

An autoclave with titanium lining provided with a high-speed rotatory agitator, gas inlet pipe and a gas out-let pipe with reflux condenser was charged with an aqueous solution of copper (II) bromide ([Cu'] = 1.012 g-atom/liter, [Br$^-$] = 1.973 g-atom/liter), and externally heated to 160° C. Through the autoclave pressurized ethylene (total ethylene pressure = 10 Kg/cm$^2$) was passed for 15 minutes and reacted under violent agitation.

Then the ethylene supply was cut off, and air was passed instead, at a total pressure of 20 Kg/cm$^2$ for 30 minutes and similarly reacted.

The above series of procedures were repeated as four cycles, and then the content of autoclave was withdrawn and analyzed. The production rate of formed ethylene glycol was 0.920 mol/l.hr., and the yield was 89.5 mol%.

During the above experiment, [Br$^-$]/[Cu'] varied with the range of 1.86–1.73 excepting the very initial period of the reaction, due to the formation and decomposition of organobromo compounds as side-products.

CONTROLS 23–26

Those Controls show the experiments in which molecular bromine was used in place of bromine ions.

The reactor similar to that used in Examples 4–12 was charged with a mixed aqueous solution of copper (II) bromide and molecular bromine, which was divided into two phases because the predominant part of the bromine was insoluble in water, and heated externally to 160° C. Through the reactor a pressurized ethylene-oxygen-nitrogen mixed gas [ethylene partial pressure (PC$_2$H$_4$) = 8.9 Kg/cm$^2$, oxygen partial pressure (PO$_2$) = 3.8[Kg/cm$^2$] was passed for an hour and reacted. The results were as shown in Table 10.

Incidentally, it is known that in the reaction as described above, the presence of copper ions, iron ions and oxygen is not essential, but the ethylene can be oxidized to form ethylene bromohydrine and ethylene dibromide, and that such products are hydrolyzed under such high temperatures as not lower than 100° C., to form ethylene glycol.

For comparison, the results of the reaction using an aqueous solution of molecular bromine alone are also given in Table 10.

Table 10

|  |  | Reaction Conditions | | | Results of Reaction Products and Production[1] (mol/l.Hr.) | | | | Ethylene Glycol Yield (mol %) |
|---|---|---|---|---|---|---|---|---|---|
|  |  | Composition of Reaction Liquid (mol/l) | | Reaction Pressure (Kg/cm²) PC₂H₄, Po₂ | Reaction Temp. (° C) | Ethylene Glycol | Ethylene Bromohydrine | Ethylene Dibromide | Miscellaneous |  |
|  |  | [CuBr₂] | [Br₂] | | | | | | | |
| Control | 23 | 0.201 | 0.512 | 8.9, 3.8 | 160 | 1.223 | 0.035 | 0.274 | 0.088 | 75.5 |
| " | 24 | 1.509 | 1.035 | 8.9, 3.8 | 160 | 1.605 | 0.074 | 1.229 | 0.562 | 46.7 |
| " | 25 | — | 1.048[2] | Ethylene alone 15.0 | 120 | 0.168 | 0.132 | 0.701 | 0.021 | 16.4 |
| " | 26 | — | 1.048[2] | Ethylene alone 15.0 | 160 | 0.585 | 0.062 | 0.110 | — | 56.6 |

[1]true production rate
[2]Br₂ disappeared at 10 minutes after the reaction started.

Regardless of the concurrent presence of copper bromide (Controls 23 and 24) or absence of copper bromide (Controls 25 and 26), in the reaction system comprising molecular bromine, first the molecular bromine very quickly disappears as the ethylene supply starts, and the product composed chiefly of ethylene dibromide is formed.

Such direct reaction of molecular bromine with ethylene, however, is a stoichiometric reaction, not the catalytic reaction. Therefore, upon the complete consumption of molecular bromine in the system, the reaction stops.

If the ethylene dibromide formed by the above reaction is left intact in the system, it gradually disappears by the reaction consisting mainly of hydrolysis, and a part thereof is converted to ethylene glycol, simultaneously forming HBr. (Note that the ethylene glycol yield in that case is low as demonstrated by Control 26.)

Thus, after the quick direct reaction of molecular bromine with ethylene at the initial stage, the reaction of copper bromide with ethylene in the concurrent presence of molecular bromine becomes substantially the equivalent to the reaction of copper bromine with ethylene in the presence of HBr, i.e., in the presence of excessive bromine ions.

As shown in Controls 23 and 24, the concurrent presence of molecular bromine in the oxidation reaction system of ethylene by copper bromide promotes the reaction in the low copper ion concentration region outside the scope of this system at which the ethylene glycol-forming rate is extremely low and not practical. However, at the copper ion concentration region specified by the invention, i.e., 0.4 g-atom/liter $\leq$ [Cu$^t$] $\leq$ 2.5 gram-atom/liter), clearly the addition of molecular bromine notably reduces the substantial production rate of ethylene glycol. Whereas, the yield (selectivity) of ethylene glycol is lowered at both of the copper ion concentration regions.

This fact can be clearly seen upon comparing, for example, the results of Control 23 with those of Control 5; or those of Control 24, with the results of Examples 10 through 12 or of Controls 7 and 8.

To wit, the use of molecular bromine is detrimental to the reaction of this invention.

EXAMPLES 46–48

The reactor similar to that used in Examples 1–3 was charged with an aqueous solution of copper bromide ([Cu$^t$] = 2.00 g-atom/liter, [Br$^-$] = 3.89 g-atom/liter), and heated to 140° C. Through the reactor propylene was fed at the initial pressure of 10 Kg/cm²G, sealed, and reacted for an hour under stirring. After the reaction, the Cu$^{++}$ ions in the aqueous solution disappeared, and 78.6 mol % to the reacted propylene of 1,2-propylene glycol was formed. The reaction liquid also contained, as the side-products, each minor amount of 1-bromopropanol-2, 1,2-dibromopropylene and acetone.

The oxidation rate of propylene was considerably greater than that of ethylene.

When the similar reaction was performed using butene-1 instead of propylene, 1,2-butylene glycol yield was 54.8%, and the oxidation rate was approximately the same to that of propylene. Also when butene-2 was used, both the yield of 2,3-butylene glycol and oxidation rate of butene-2 were still lower than those with butene-1. In both cases side-production of methyl ethyl ketone was observed.

We claim:

1. A process for making glycols comprising contacting an aliphatic olefin with 2–4 carbon atoms with an aqueous medium containing
   i. at least one cation selected from the group consisting of copper ions and iron ions, and
   ii. an anion which at least includes a bromine ion and can solubilize copper and/or iron at 100°–200° C., to form a glycol corresponding to the starting olefin, which is characterized in that the concentrations of the cation and anion and the ratio therebetween are controlled to satisfy the following conditions:

I. when the cation in the aqueous medium is a copper ion, $$0.4 \leq [Cu^t] \leq 2.5 \tag{1}$$

$$0.8 \leq [Br^-] \leq 4.0 \tag{2}$$

$$1.75 [Cu^t] \leq [A^t] \leq 2.0 [Cu^t] \tag{3}$$

$$0.8 [Cu^t] \leq [Br^-] \leq 1.95 [Cu^t] \tag{4}$$

II. when the cation in the aqueous medium is an iron ion, $$0.3 \leq [Fe^t] \leq 2.0 \tag{5}$$

$$0.5 \leq [Br^-] \leq 6.0 \tag{6}$$

$$2.0 [Fe^t] \leq [A^t] \leq 3.0 [Fe^t] + 4.0 \tag{7}$$

$$1.0 [Fe^t] \leq [Br^-] \leq 3.0 [Fe^t] + 1.0 \tag{8}$$

and

III. when the cation in the aqueous medium consists of copper and iron ions, $$0.05 \leq [Cu^t] + [Fe^t] \leq 1.6 \quad (9)$$

$$0.01 \leq [Cu^t] \quad (10)$$

$$0.01 \leq [Fe^t] \quad (11)$$

$$0.5 \leq [Br^-] \leq 4.0 \quad (12)$$

$$2.0\{[Cu^t]+[Fe^t]\} \leq [A^t] \leq 3.5\{[Cu^t]+[Fe^t]\} + 4.0 \quad (13)$$

$$1.0\{[Cu^t]+[Fe^t]\} \leq [Br^-] \leq 3.5\{[Cu^t]+[Fe^t]\} \quad (14)$$

provided that, in the foregoing formulae (1) through (14), $[Cu^t]$, $[Br^-]$, $[A^t]$ and $[Fe^t]$ respectively denotes the total ion concentration per liter of the aqueous medium, $[Cu^t]$ being the total ion concentration (gram-atom/liter) of ionized copper ($Cu^+$ and $Cu^{++}$)

$[Br^-]$ being the total ion concentration gram-atom/liter of the bromine ion which can solubilize copper and/or iron, $[A^t]$ being the total ion concentration (gram-ionic equivalent/liter) of the anion which at least includes a bromine ion and can solubilize copper and/or iron, all calculated as converted to monovalent anions, and $[Fe^t]$ being the total ion concentration (gram-atom/liter) of ionized iron ($Fe^{++}$ and $Fe^{+++}$).

2. The process for making glycols according to claim 1, wherein the contact of the aliphatic olefin with the aqueous medium is effected in the presence of molecular oxygen.

3. The process for making glycols according to claim 1, wherein the glycol-containing reaction mixture obtained upon contacting the aliphatic olefin with the aqueous medium is contacted with molecular oxygen in a vessel identical or different from the first reactor.

4. The process for making glycols acording to claim 1, wherein at least a part of the glycol-containing reaction mixture obtained upon contacting the aliphatic olefin with the aqueous medium is contacted with molecular oxygen in a vessel different from the first reactor, and at least a part of the reaction mixture contacted with molecular oxygen is recycled into the contacting system of the olefin with the aqueous medium.

5. The process acccording to claim 1, wherein, when the aqueous medium contains as the cations
(I) copper ions, or
(III) copper ions and iron ions,
the contact of the aqueous medium with the aliphatic olefin is effected at 140°–180° C.

6. The process according to claim 1, wherein, when the aqueous medium contains as the cation
(II) iron ions,
the contact of the aqueous medium with the aliphatic olefin is effected at 120°–180° C.

7. The process for making glycols according to claim 1, wherein the contact of the aliphatic olefin with the aqueous medium is effected, while controlling the concentrations of cations and anions and the ratio therebetween to satisfy the conditions specified below:

I. when the cations in the aqueous medium are copper ions, $$0.6 \leq [Cu^t] \leq 1.6 \quad (1a)$$

$$0.9 \leq [Br^-] \leq 3.0 \quad (2A)$$

$$1.80[Cu^t] \leq [A^t] \leq 1.95[Cu^t] \quad (3a)$$

$$1.2[Cu^t] \leq [Br^-] \leq 1.90[Cu^t] \quad (4a)$$

II. when the cations in the aqueous medium are iron ions, $$0.4 \leq [Fe^t] \leq 1.5 \quad (5a)$$

$$0.7 \leq [Br^-] \, 4.0 \quad (6a)$$

$$2.1[Fe^t] \leq [A^t] \leq 3.0[Fe^t] + 3.0 \quad (7a)$$

$$1.0[Fe^t] \leq [Br^-] \leq 3.0[Fe^t] + 0.5 \quad (8a)$$

and (III) when the cations in the aqueous medium are copper and iron ions, $$0.2 \leq [Cu^t] + [Fe^t] \leq 1.4 \quad (9a)$$

$$0.05 \leq [Cu^t] \leq 0.8 \quad (10a)$$

$$0.2 \leq [Fe^t] \quad (11a)$$

$$0.5 \leq {}^l[Br^-] \leq 3.5 \quad (12a)$$

$$2.05\{[Cu^t]+[Fe^t]\} \leq [A^t] \leq 3.5\{[Cu^t]+[Fe^t]\} + 2.5 \quad (13a)$$

$$1.1\{[Cu^t]+[Fe^t]\} \leq [Br^-] \leq 3.2\{[Cu^-]+[Fe^t]\} \quad (14a)$$

provided that the definitions of $[Cu^t]$, $[Br^-]$, $[A^t]$ and $[Fe^t]$ in the formulae (1a) through (14a) are same to those given as to the formulae (1) through (14) in claim 1.

8. The process for making glycols according to claim 1, in which the contact of the aliphatic olefine with the aqueous medium is effected while controlling the concentrations of cations and anions and the ratio therebetween in the aqueous medium to satisfy the following conditions:

I. when the cations in the aqueous medium are iron ions, $$0.5 \leq [Fe^t] \leq 1.2 \quad (5b)$$

$$1.0 \leq [Br^-] \leq 3.0 \quad (6b)$$

$$2.2[Fe^t] \leq [A^t] \leq 3.0[Fe^t] + 2.0 \quad (7b)$$

$$1.2[Fe^t] \leq [Br^-] \leq 3.0[Fe^t] \quad (8b)$$

II. when the cations in the aqueous medium are copper ions and iron ions, $$0.4 \leq [Cu^t] + [Fe^t] \leq 1.2 \quad (9b)$$

$$0.10 \leq [Cu^t] \leq 0.4 \quad (10b)$$

$$0.4 \leq [Fe^t] \quad (11b)$$

$$1.0 \leq [Br^-] \leq 3.0 \quad (12b)$$

$$2.10\{[Cu^t]+[Fe^t]\} \leq [A^t] \leq 3.5\{[Cu^t]+[Fe^t]\} + 1.5 \quad (13b)$$

$$1.2\{[Cu^t]+[Fe^t]\} \leq [Br^-] \leq 3.0\{[Cu^t]+[Fe^t]\} \quad (14b)$$

provided that the definitions of $[Cu^t]$, $[Br^-]$, $[A^t]$ and $[Fe^t]$ in the above formulae (5b) through (14b) are the same to those given as to the formulae (1) through (14) in claim 1.

9. The process for making glycols according to claim 1, in which the aliphatic olefin is ethylene.

10. The process for making glycols according to claim 1, in which the aliphatic olefin is propylene.

11. The process for making glycols according to claim 1, in which the aqueous medium contains the copper ions and bromine ions supplied from at least one compound selected from the group consisting of $CuBr_2$, $CuBr$, and $CuBr_2 \cdot 3Cu(OH)_2$.

12. The process for making glycols according to claim 1, in which the aqueous medium contains the iron ions and bromine ions supplied from at least one compound selected from the group consisting of $FeBr_3$ and $FeBr_2$.

13. The process for making glycols according to claim 1, in which the aqueous medium contains, as the anions including a bromine ion and being capable of solubilizing copper and/or iron, at least one member of the group consisting of bromine ion, sulfate ion, borate ion, phosphate ion, acetate ion and halogenoacetate ions.

* * * * *